（12） United States Patent
Hartmann

(10) Patent No.: US 12,364,819 B2
(45) Date of Patent: Jul. 22, 2025

(54) FLUIDIC SUBSYSTEM FOR MULTI-USE DRUG-DELIVERY DEVICE

(71) Applicant: Eli Lilly and Company, Indianapolis, IN (US)

(72) Inventor: Daniel Morris Hartmann, Arlington, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 874 days.

(21) Appl. No.: 17/310,503

(22) PCT Filed: Feb. 5, 2020

(86) PCT No.: PCT/US2020/016699
§ 371 (c)(1),
(2) Date: Aug. 6, 2021

(87) PCT Pub. No.: WO2020/167537
PCT Pub. Date: Aug. 20, 2020

(65) Prior Publication Data
US 2022/0088308 A1    Mar. 24, 2022

Related U.S. Application Data

(60) Provisional application No. 62/804,364, filed on Feb. 12, 2019.

(51) Int. Cl.
*A61M 5/20* (2006.01)
*A61M 5/00* (2006.01)
*A61M 5/142* (2006.01)

(52) U.S. Cl.
CPC ............ *A61M 5/20* (2013.01); *A61M 5/002* (2013.01); *A61M 5/008* (2013.01);
(Continued)

(58) Field of Classification Search
CPC ........ A61M 5/20; A61M 5/002; A61M 5/008; A61M 5/14248; A61M 5/158;
(Continued)

(56) References Cited

U.S. PATENT DOCUMENTS 5,735,818 A * 4/1998 Kriesel ................. A61M 5/152
604/246
7,780,636 B2 8/2010 Radmer et al.
(Continued)

FOREIGN PATENT DOCUMENTS

WO      2010084113        7/2010
WO      WO-2010084113 A1 * 7/2010 ............ A61M 5/204

OTHER PUBLICATIONS

Patent Cooperation Treaty Written Opinion of the International Searching Authority pertaining to International Application No. PCT/2020/016699; International Filing Date: Feb. 5, 2020; Date of Mailing: Apr. 28, 2020.

(Continued)

*Primary Examiner* — Nathan R Price
*Assistant Examiner* — Haden Matthew Ritchie
(74) *Attorney, Agent, or Firm* — Arthur Shum

(57) ABSTRACT

The present disclosure relates to drug-delivery apparatuses, and in particular, to a drug-delivery apparatus with a fluidic subsystem that can be used to deliver multiple injections to a patient from a drug container storing a drug fluid. The fluidic subsystem may include multiple injection-needle compartments and re-sealable septa to allow multiple accesses to the drug container, while also preserving the sterility of the drug fluid and of the fluid pathway through which the fluid is delivered to a patient. In some embodiments, the fluidic subsystem may be used to deliver drug fluids that do not contain any preservatives (e.g., non-preserved drugs).

15 Claims, 8 Drawing Sheets

(52) U.S. Cl.
CPC ... *A61M 5/14248* (2013.01); *A61M 2005/004* (2013.01); *A61M 2005/206* (2013.01); *A61M 2205/12* (2013.01)

(58) Field of Classification Search
CPC .............. A61M 5/3232; A61M 5/1409; A61M 2005/004; A61M 2005/206; A61M 2205/12; A61M 2005/14252; A61M 2005/1581
See application file for complete search history.

(56) References Cited

U.S. PATENT DOCUMENTS

| | | |
|---|---|---|
| 8,057,434 B2 | 11/2011 | Burroughs et al. |
| 8,216,192 B2 | 7/2012 | Burroughs et al. |
| 8,696,570 B2 | 4/2014 | Yodfat et al. |
| 9,149,578 B2 | 10/2015 | Byerly et al. |
| 9,889,249 B2 | 2/2018 | Steel et al. |
| 9,981,088 B2 | 5/2018 | Byerly |
| 2010/0152660 A1 | 6/2010 | Mack et al. |
| 2010/0312195 A1* | 12/2010 | Johansen ............ A61M 5/2033 604/192 |
| 2012/0130313 A1* | 5/2012 | Byerly .................... A61M 5/20 604/173 |
| 2014/0332425 A1 | 11/2014 | Hofmann et al. |
| 2019/0360902 A1* | 11/2019 | Darsigny ............... G01N 21/76 |
| 2021/0244884 A1* | 8/2021 | Schabbach ............ A61M 5/282 |

OTHER PUBLICATIONS

Patent Cooperation Treaty International Search Report pertaining to International Application No. PCT/2020/016699; International Filing Date: Feb. 5, 2020; Date of Mailing: Apr. 28, 2020.

* cited by examiner

FLUIDIC SUBSYSTEM FOR MULTI-USE DRUG-DELIVERY DEVICE

FIELD OF THE DISCLOSURE

The present disclosure relates to drug-delivery apparatuses, and in particular, to fluidic subsystems for a drug-delivery apparatus that can be used to deliver multiple injections to a patient from a drug container storing a drug fluid.

BACKGROUND

Drug-delivery devices such as auto-injectors and bolus injectors are often used to dispense drug formulations that do not have preservatives in them. To ensure the sterility of the drug, such devices are commonly single-use; the entire contents of the drug-delivery device is delivered at one time and the device is then discarded.

SUMMARY

The present disclosure relates to drug-delivery apparatuses having a fluidic subsystem for conveying a drug liquid from a drug container, through a fluid path within the apparatus, and into the patient. In particular, the fluidic subsystem and/or drug-delivery apparatus may be used to deliver multiple injections to a patient.

According to an exemplary embodiment of the present disclosure, an apparatus is provided for delivering multiple injections of a pharmaceutical liquid to a patient, comprising: a needle magazine including a body defining a plurality of injection needle compartments that are each sealed in an air-tight manner from each other and from external atmosphere, each injection needle compartment comprising (i) a needle assembly having an injection needle and an associated septum piercing needle spaced apart from the injection needle and in fluid communication with the injection needle, and (ii) a compartment septum associated with the needle assembly and configured to be pierced by the septum piercing needle; a drug container containing the pharmaceutical liquid, the drug container in fluid communication with a drug fluid pathway; a drug container septum that separates the drug fluid pathway from an intermediate pathway that leads to the needle magazine; and a drive assembly configured to, when actuated, drive a needle assembly of one of the injection needle compartments such that the injection needle of the driven needle assembly extends from the needle magazine and into a patient, and such that the septum piercing needle of the driven needle assembly pierces the compartment septum associated with the driven needle assembly, traverses the intermediate pathway, and pierces the drug container septum to access the drug fluid pathway, thereby creating a fluid pathway from the drug container to an outlet of the injection needle.

In one example, the compartment septum associated with the driven needle assembly is configured to isolate the intermediate pathway and the drug container septum from atmosphere within the injection needle compartment when the compartment septum associated with the driven needle assembly is pierced by the septum piercing needle.

In another example, the drive assembly is further configured to withdraw the driven needle assembly such that the injection needle of the driven needle assembly is withdrawn out of the patient and the septum piercing needle of the driven needle assembly is withdrawn out of both the drug container septum and the compartment septum associated with the driven needle assembly.

In another example, the needle magazine comprises a round, rotatable body that is configured to rotate after the driven needle assembly has been withdrawn so as to position another needle assembly in another injection needle compartment to be driven by the drive assembly.

In another example, the rotatable body of the needle magazine is disposed on top of a magazine seat that comprises an inner O-ring and an outer O-ring that ensure each injection needle compartment in the needle magazine remains sealed from external atmosphere before use.

In another example, the needle magazine body comprises a linear body that is configured to translate after the driven needle assembly has been withdrawn so as to position another needle assembly in another injection needle compartment to be driven by the drive assembly.

In another example, the compartment septum in each injection needle compartment is configured to be pierced only once before the apparatus is discarded.

In another example, the drug container septum is configured to be pierced multiple times before the apparatus is discarded.

In another example, the drug container septum is configured to be pierced once by the septum piercing needle of the needle assembly in each injection needle compartment before the apparatus is discarded.

In another example, each injection needle compartment, the drug fluid pathway, and the intermediate pathway have been sterilized.

In another example, each injection needle compartment further comprises a flexible cover that is configured to flex but not break to allow the drive assembly to drive the needle assembly in said injection needle compartment while ensuring said needle injection needle compartment remains sealed from external atmosphere.

In another example, each injection needle compartment further comprises a separate frangible sterility film that seals each respective injection needle compartment from external atmosphere, and wherein the drive assembly is configured to drive the driven needle assembly such that the injection needle of the driven needle assembly breaks the frangible sterility film of the injection needle compartment of the driven needle assembly.

In another example, the needle magazine further comprises an injection-needle septum that isolates an interior portion of the injection needle compartment of the driven needle assembly and the septum piercing needle of the driven needle assembly from external atmosphere when the frangible sterility film of the injection needle compartment of the driven needle assembly is broken by the injection needle of the driven needle assembly.

In another example, each injection needle compartment further comprises a separate sterility film that is configured to be peeled away by a user, wherein each sterility film seals each respective injection needle compartment from external atmosphere.

In another example, the pharmaceutical liquid comprises a drug that does not contain any preservatives.

Figure 1:
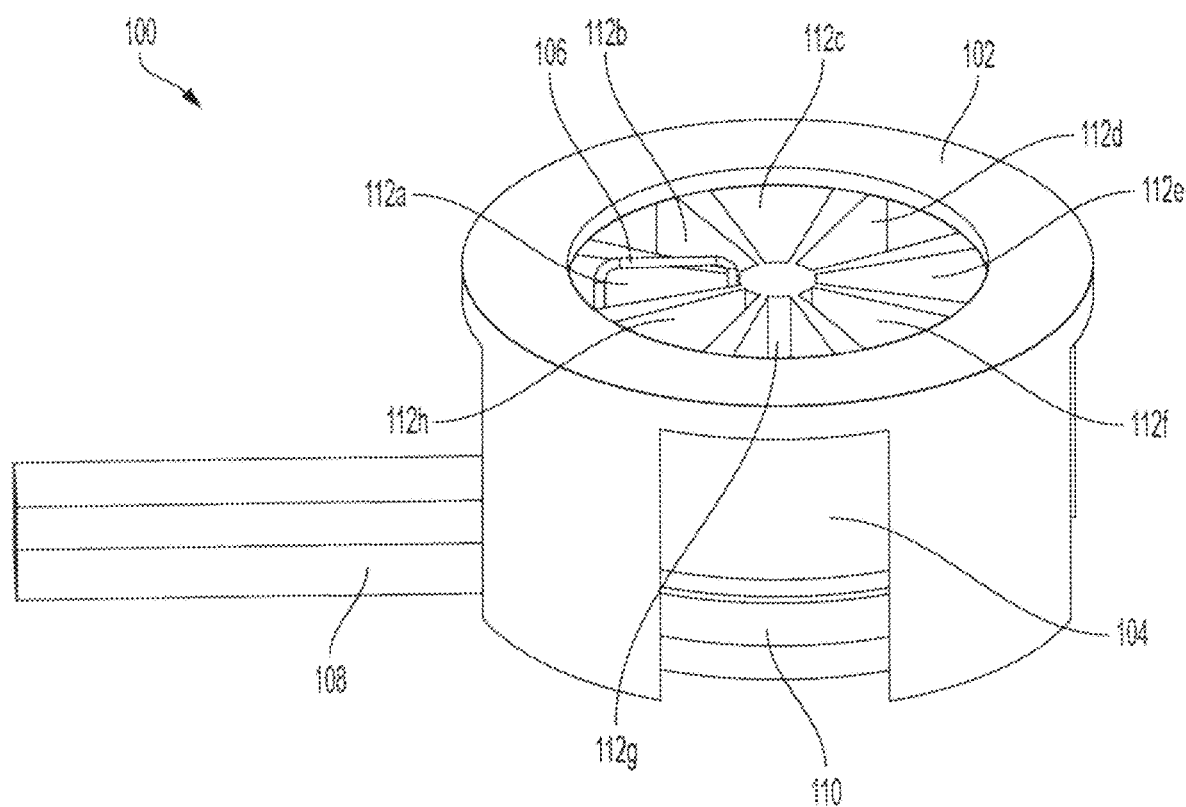
FIG. 1 provides a perspective view of a fluidic subsystem for use with a drug-delivery apparatus, in accordance with at least one embodiment.

Corresponding reference characters indicate corresponding parts throughout the several views. Although the exemplification set out herein illustrates embodiments of the present disclosure, in several forms, the embodiments disclosed below are not intended to be exhaustive or to be construed as limiting the scope of the invention to the precise forms disclosed.

DETAILED DESCRIPTION

The present disclosure relates to drug-delivery apparatuses that comprise a fluidic subsystem. The fluidic subsystem may be configured to deliver multiple injections of a drug fluid from a drug container. The fluidic subsystem may be configured to allow access to the drug container multiple times to enable multiple injections over an extended period of time (e.g., multiple days, weeks, or months), while also preserving the sterility of the drug fluid stored within the drug container and of the fluid pathway through which the drug fluid is delivered to a patient. As a result, the fluidic subsystem may be used to deliver drug fluids that do not have any preservatives in them (i.e., non-preserved drug formulations) as well as preserved drugs. Compared to drug-delivery apparatuses that can only deliver one dose and then must be discarded, such a multi-use drug-delivery apparatus may be less costly and/or more convenient to use, and may also be more environmentally responsible.

The disclosed fluidic subsystems and drug-delivery apparatuses may comprise a drug and/or a pharmaceutical liquid. In some embodiments, a system may comprise one or more devices, including the disclosed fluidic subsystems and drug-delivery apparatuses, and a drug and/or pharmaceutical liquid. The term "drug" and/or "pharmaceutical liquid" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies including but not limited to IL-23 antibody analogs or derivatives, such as mirikizumab, IL-17 antibody analogs or derivatives, such as ixekizumab, therapeutic agents for pain related treatments, such as galcanezumab or lasmiditan, and any therapeutic agent that is capable of delivery by the disclosed fluidic subsystems and/or drug-delivery apparatuses.

According to some embodiments, the fluidic subsystem may comprise a rotating needle magazine having multiple injection-needle compartments, each compartment storing a separate needle assembly. The interior volume of each compartment and the needle assembly within may be sterilized during assembly or manufacturing and sealed from external atmosphere. In some embodiments, each needle assembly is configured for use in a single injection only. The rotating needle magazine is mechanically indexed to align one of its injection-needle compartments with a drug-delivery path. When aligned, a drive assembly may be actuated to drive the needle assembly within the aligned injection-needle compartment to inject the patient. After the injection, the drive assembly (or another component within the drug-delivery apparatus) withdraws the needle assembly back into the injection-needle compartment. The needle magazine may then be mechanically rotated (e.g. by one or more gears) to move the used needle assembly out of the drug-delivery path and position a new, unused needle assembly of another injection-needle compartment in its place. When all the needle assemblies in the needle magazine have been used, the needle magazine, fluidic subsystem, or the entire drug-delivery apparatus of which the fluidic subsystem is a part may be discarded.

The fluidic subsystem may further comprise one or more of a plurality of compartment septa, an injection-needle septum, and a drug container septum. These components work together to preserve the sterility of a drug stored in a drug container, as well as of a drug fluid pathway and intermediate pathway that conveys the stored drug fluid to the needle magazine throughout multiple injections. Each septum may comprise a membrane or stopper that provides an airtight seal, preventing the passage of atmosphere or fluid, but which is able to be pierced by sharp needles or cannulae. Once pierced by a sharp needle or cannula, a septum may be configured to provide an air-tight seal around the needle or cannula so that no atmosphere or fluid may pass around the penetrating needle or cannula. When the needle or cannula is withdrawn from a septum, the septum may close behind the needle or cannula to re-establish its previous airtight seal. For septa designed to be pierced only once, such as the compartment septa described below, suitable materials for use in the septa include chlorobutyl and/or bromobutyl rubber. For a septum designed to be pierced multiple times, such as the injection-needle septum described below, the septum may comprise two or more layers comprising chlorobutyl and/or bromobutyl rubber and isoprene. Since the fluidic subsystem maintains the sterility of the drug container and drug fluid pathway throughout multiple injections, the fluidic subsystem may be used to deliver multiple injections of a non-preserved drug.

FIG. 1 provides a perspective view of a fluidic subsystem 100 for use within or in conjunction with an apparatus for delivering multiple injections of a pharmaceutical liquid to a patient in accordance with one embodiment. Fluidic subsystem 100 includes a needle magazine 104 that is held in place on top of a magazine seat 110 by a magazine retainer 102 while being rotatable relative to magazine seat 110 and magazine retainer 102. Needle magazine 104 comprises a round, rotatable body that defines a plurality of parallel injection needle compartments denoted as 112a, 112b, 112c, 112d, 112e, 112f, 112g, and 112h. Although FIG. 1 depicts eight injection needle compartments, there may be more or fewer compartments. As explained in further detail below, each injection needle compartment is sealed in an air-tight manner from each other and from external atmosphere. In FIG. 1 however, the flexible cover 406 (shown in FIG. 4) that seals the top of each injection needle compartment has been removed to illustrate the interior of each injection needle compartment. Each injection needle compartment 112a-h houses a needle assembly 106—although only one needle assembly 106 is shown within injection needle compartment 112a, it should be understood that each needle compartment 112a-h includes a similar needle assembly. A drug container conduit 108 connects to the magazine seat 110 as shown.

Figure 2:
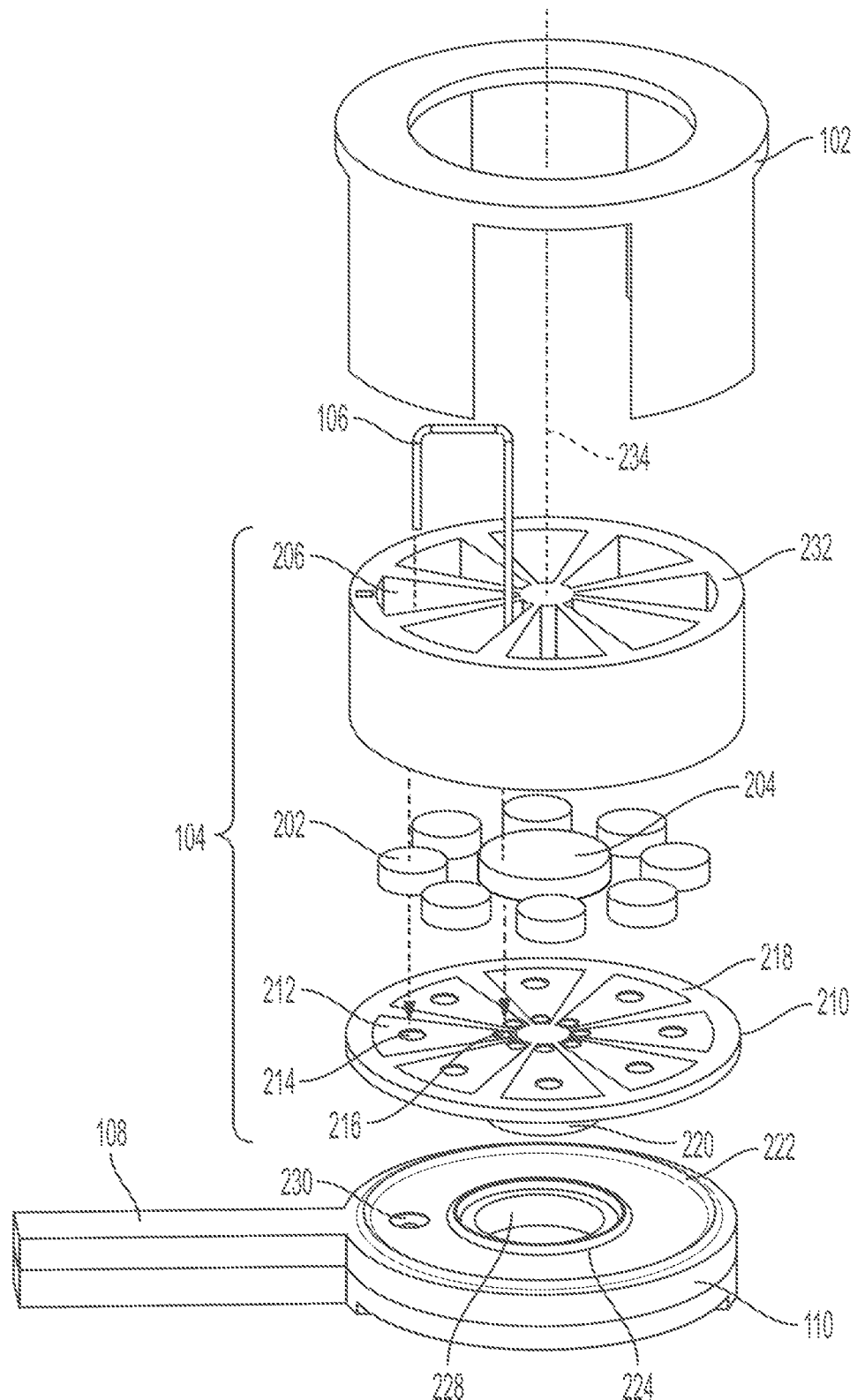
FIG. 2 provides an exploded perspective view of the fluidic subsystem of FIG. 1, in accordance with at least one embodiment.

FIG. 2 provides an exploded perspective view of the fluidic subsystem 100. As shown, needle magazine 104 comprises several sub-components, including a magazine top 232, an injection-needle septum 204, a plurality of separate compartment septa 202, and a magazine bottom 210. Needle magazine 104 and its sub-components are configured to rotate about axis of rotation 234. Magazine top 232 includes a plurality of magazine top cavities 206 that define the side walls of each injection needle compartment 112a-h. Injection-needle septum 204 is positioned below the center of magazine top 232. The plurality of separate compartment septa 202 include one separate compartment septum corresponding to each injection needle compartment 112a-h—each separate compartment septum is associated with the needle assembly disposed in said each injection needle compartment. Magazine bottom 210 comprises a magazine bottom plate 218 and a magazine bottom hub 220. Magazine bottom plate 218 includes a plurality of sections 212—each section 212 includes a septum-piercing-needle hole 214 and an injection-needle hole 216 spaced radially inwardly from hole 214. Each septum-piercing-needle hole 214 defines a passage from a top side of magazine bottom plate 218 to a bottom side of magazine bottom plate 218. Similarly, each injection-needle hole 216 defines a passage from a top side of magazine bottom plate 218 to a bottom side of magazine bottom hub 220. When assembled, magazine top 232 is attached to magazine bottom plate 218 of magazine bottom 210 (e.g., via a laser weld, adhesive, or ultrasonic weld), with injection-needle septum 204 and compartment septa 202 inserted between magazine top 232 and magazine bottom plate 218. Each compartment septum 202 is aligned with one of the septum-piercing-needle holes 214, and the injection-needle septum 204 is positioned so as to cover the injection-needle holes 216.

Needle magazine 104 sits on top of magazine seat 110. Magazine bottom hub 220 of magazine bottom 210 is configured to fit within magazine seat recess 228 such that needle magazine 104 may rotate within recess 228 relative to magazine seat 110. Magazine seat 110 further comprises a fluid hole 230 through which, as described in further detail below, a pharmaceutical liquid from a drug container may be accessed. The top surface of magazine seat 110 comprises an inner O-ring 224 and an outer O-ring 222.

Figure 3:
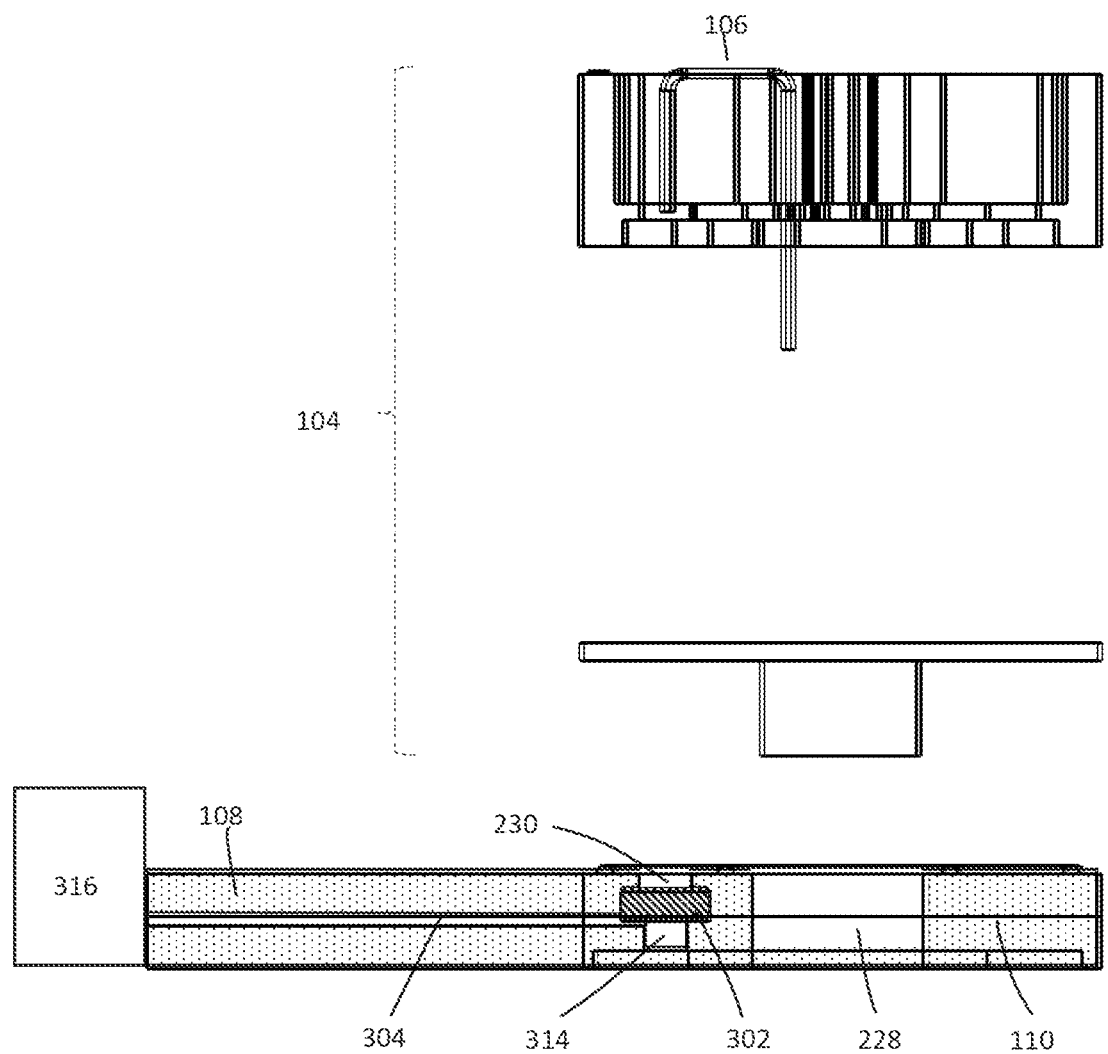
FIG. 3 provides an exploded, profile, cross-sectional view of the fluidic subsystem of FIG. 1, in accordance with at least one embodiment.

FIG. 3 provides an exploded, profile, cross-sectional view of fluidic subsystem 100. To simplify the figure, magazine retainer 102 has been omitted and only one compartment septum 202 and only one needle assembly 106 have been displayed. It should be understood, however, that there may be one compartment septum 202 and one needle assembly 106 corresponding to each magazine top cavity 206 and each injection needle compartment 112a-h. As shown in the cross-sectional view of FIG. 3, fluid hole 230 in magazine seat 110 leads to a drug container septum 302. Drug container septum 302 is disposed between fluid hole 230 and a drug fluid chamber 314. Drug fluid chamber 314 is in fluid communication with a drug container 316 via a drug fluid conduit 304. Together, drug fluid chamber 314 and drug fluid conduit 304 comprise a drug fluid pathway. In some embodiments, the drug fluid pathway may further comprise a pumping mechanism (not shown) that pumps drug fluid from the drug container 316 along the drug fluid pathway. Such a pumping mechanism may comprise a push pump that pushes on a movable component in the drug container 316, or may be a "pull-push" system that pulls liquid out of the drug container 316 before pushing it forward. Any other suitable pumping mechanism may be provided. The interior surfaces of the drug fluid pathway may be sterilized during manufacture and assembly. Drug container 316 may comprise any container that holds a drug fluid in storage—such a container may be provided to patients or caregivers pre-filled with the drug fluid, or may be manually configured to be filled by patients or caregivers. Drug container 316 may comprise a rigid container, such as a glass cartridge or syringe, or a container having one or more flexible walls.

Figure 4:
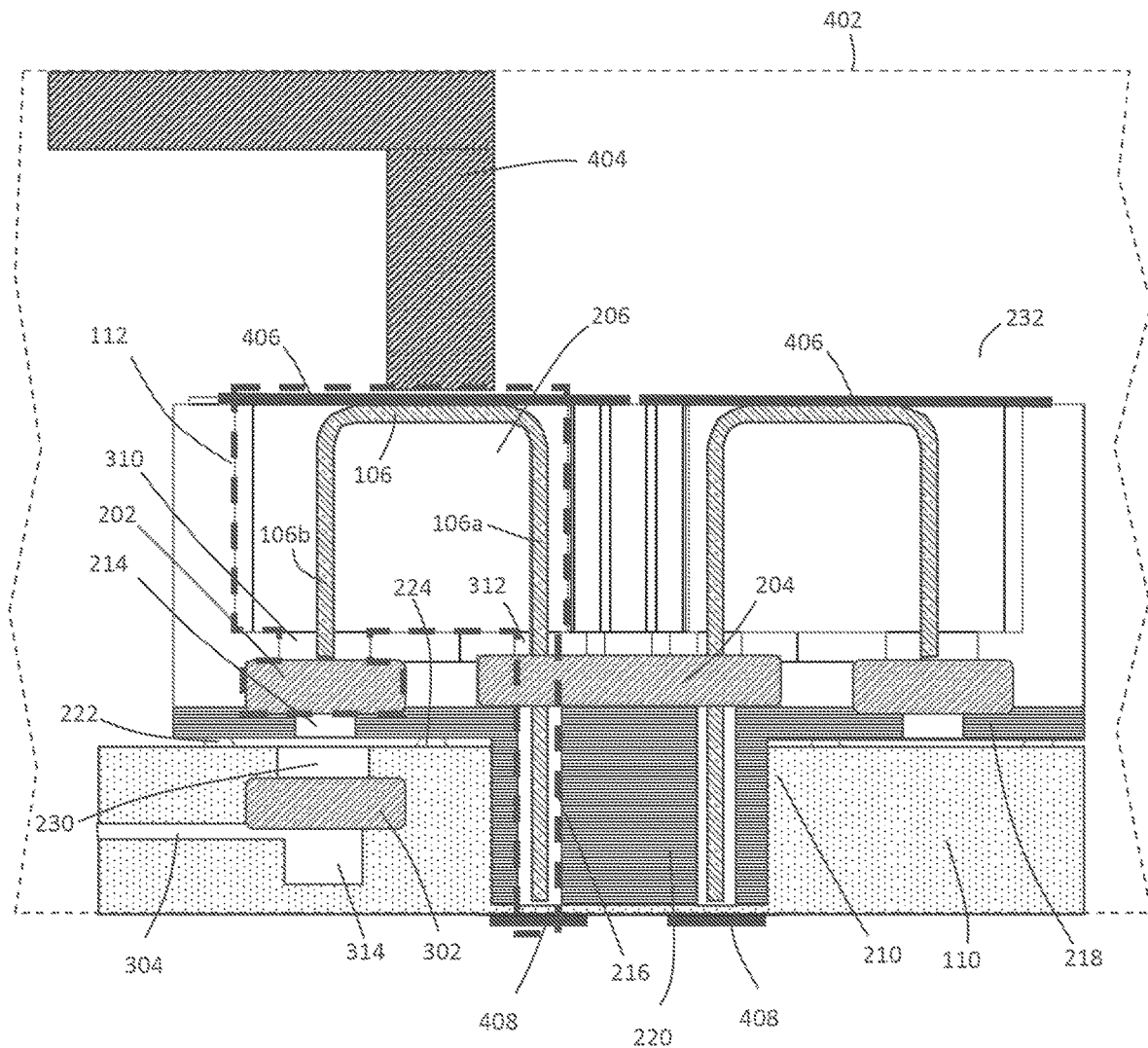
FIG. 4 provides a profile, cross-sectional view of the fluidic subsystem of FIG. 1 before it has been actuated to inject a patient, in accordance with at least one embodiment.

FIG. 4 provides a profile, cross-sectional view of fluidic subsystem 100 before it has been actuated to inject a patient. Fluidic subsystem 100 may be arranged within an outer casing 402, shown in light dashed lines. In addition to the components described previously, FIG. 4 depicts a plurality of frangible sterility films 408 attached to the bottom of hub 220. Each frangible sterility film 408 covers the bottom outlet of one of the injection-needle holes 216. FIG. 4 also includes a plurality of flexible covers 406—each flexible cover 406 covers the top side of one of the magazine top cavities 206. An injection-needle compartment 112 (referenced in FIG. 1 as 112a-h, and indicated using a bolded dashed line in FIG. 4) may be defined at least-in-part by the interior volume defined by a magazine top cavity 216, a flexible cover 406, an injection-needle hole 216, a frangible sterility film 408, and a compartment septum 202. Together, these components maintain an air-tight seal that separates each injection-needle compartment 112 from each other as well as from external atmosphere. Within each injection-needle compartment 112 is disposed a needle assembly 106. Each needle assembly 106 comprises an injection needle 106a and an associated, parallel septum-piercing needle 106b that is in fluid communication with the injection needle 106a. In some embodiments, the two parallel needles are part of a monolithic U-shaped or J-shaped needle. Before fluidic subsystem 100 is actuated, the injection needle 106a pierces injection-needle septum 204 and is at least partially disposed within injection-needle hole 216, while the septum-piercing needle 106b is disposed proximate to, but does not pierce, the compartment septum 202 associated with that injection-needle compartment 112. The interior of each injection-needle compartment 112, as well as the needle assembly 106 disposed within each injection-needle compartment, is sterilized. The air-tight seal provided by frangible sterility film 408, flexible cover 406, and compartment septum 202 prevents external atmosphere or contaminants from entering an injection-needle compartment, thus preserving the sterility of each compartment and its needle assembly.

Needle magazine 104 (shown in FIGS. 2-3) may be biased downwards against the top surface of magazine seat 110. This biasing force may be provided by, for example, magazine retainer 102 (not shown in FIG. 4). This biasing force pushes the underside of magazine bottom plate 218 against the inner O-ring 224 and an outer O-ring 222 arranged on the top surface of magazine seat 110—both O-rings are shown in profile in FIG. 4.

Needle magazine 104 is also mechanically indexed by one or more gears, detents, tabs, or grooves such that one of the injection-needle compartments 112 aligns with a drive assembly 404 and fluid hole 230 in magazine seat 110. Exemplary mechanisms suitable for mechanically indexing and/or rotating needle magazine 104 are disclosed in U.S. Pat. No. 8,057,434 and U.S. Patent App. Pub. No. 2010/0152660, both of which are incorporated herein by reference in their entirety. When aligned, drive assembly 404 is positioned to drive needle assembly 106 within the aligned injection needle compartment, as described in further detail below in relation to FIGS. 5-7. Also when aligned, the septum-piercing-needle hole 214 and compartment septum 202 corresponding to the aligned injection-needle compartment is positioned on top of fluid hole 230. Septum-piercing-needle hole 214, inner O-ring 224, outer O-ring 222, and fluid hole 230 together define an intermediate pathway between drug container septum 302 and the compartment septum 202 of the aligned injection needle compartment 112. Inner O-ring 224 and outer O-ring 222 maintain an air-tight seal that separates the interior volume defined by the two O-rings, the underside of magazine bottom plate 218, and the top surface of magazine seat 110 from external atmosphere. This interior volume is also sterilized during assembly, and the air-tight seal provided by the O-rings 222 and 224 maintain said sterility by preventing external atmosphere or contaminants from entering this space.

Figure 5:
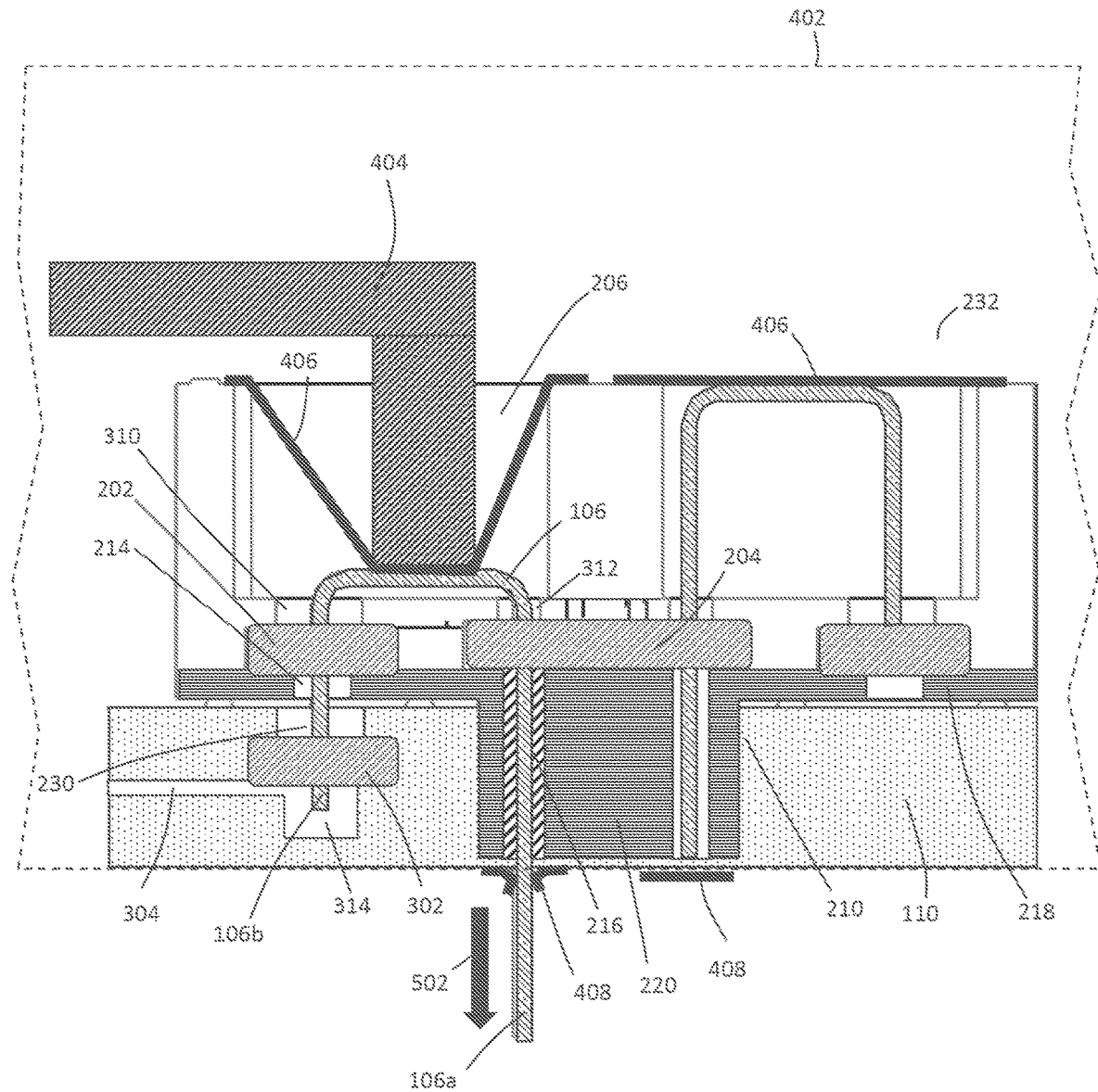
FIG. 5 provides a profile, cross-sectional view of the fluidic subsystem of FIG. 1 after it has been actuated to inject a patient, but before the injection needle is withdrawn, in accordance with at least one embodiment.

FIG. 5 provides a profile, cross-sectional view of fluidic subsystem 100 after it has been actuated to inject a patient, but before the injection needle is withdrawn. When the fluidic subsystem is actuated, drive assembly 404 drives needle assembly 106 downwards in the direction of arrow 502. Although drive assembly 404 is depicted as a hammer-shaped element that translates downwards, drive assembly 404 may take other shapes and forms or translate or pivot in different directions—examples of suitable drive assemblies and needle assemblies may be found in the previously-mentioned U.S. Pat. No. 8,057,434 and U.S. Patent Application Pub. No. 2010/0152660, both of which are incorporated herein in their entirety. When drive assembly 404 drives needle assembly 106 downwards, flexible cover 406, which may be made of an elastic material, may flex but not break to ensure that its air-tight seal over the top of magazine top cavity 206 is preserved. As needle assembly 106 is driven downwards, the injection needle 106a breaks the frangible sterility film 408 and protrudes partially out of the outer casing 402 and into a patient (not shown). Also as needle assembly 106 is driven downwards, the septum-piercing needle 106b pierces the compartment septum 202 associated with the driven needle assembly, traverses the intermediate pathway defined by septum-piercing-needle hole 214, inner O-ring 224, outer O-ring 222, and fluid hole 230, and pierces the drug compartment septum 302. This allows the septum-piercing needle 106b to access the drug fluid chamber 314, thereby creating a fluid pathway from the drug container 316 (shown in FIG. 3) into the patient (not shown). Drug fluid then flows from the drug container 316, through the drug fluid pathway, and through the needle assembly 106 into the patient. Since the drug fluid flows away from the drug container, no external contaminants are permitted to flow from the patient or external environment back into the drug fluid pathway, thereby preserving the sterility of the drug fluid pathway and drug container.

When injection needle 106a breaches the frangible sterility film 408, injection-needle hole 216 will be exposed to external atmosphere. In this embodiment, the interior of injection-needle hole 216 may no longer be considered sterile, as indicated by the bolded hashing within injection-needle hole 216 in FIG. 5. However, injection-needle septum 204 maintains an air-tight seal around injection needle 106a, such that external atmosphere may not enter the interior of magazine top cavity 206 and contaminate septum-piercing needle 106b before it is driven through compartment septum 202, the intermediate pathway, and/or the drug container septum 302. Similarly, the air-tight seal provided by flexible cover 406 ensures external atmosphere may not enter magazine top cavity 206 and contaminate any portion of septum-piercing needle 106b before it is driven through compartment septum 202, the intermediate pathway, and/or the drug container septum 302. Ensuring the sterility of septum-piercing needle 106b helps ensure the sterility of the intermediate pathway and the drug fluid pathway.

Figure 6:
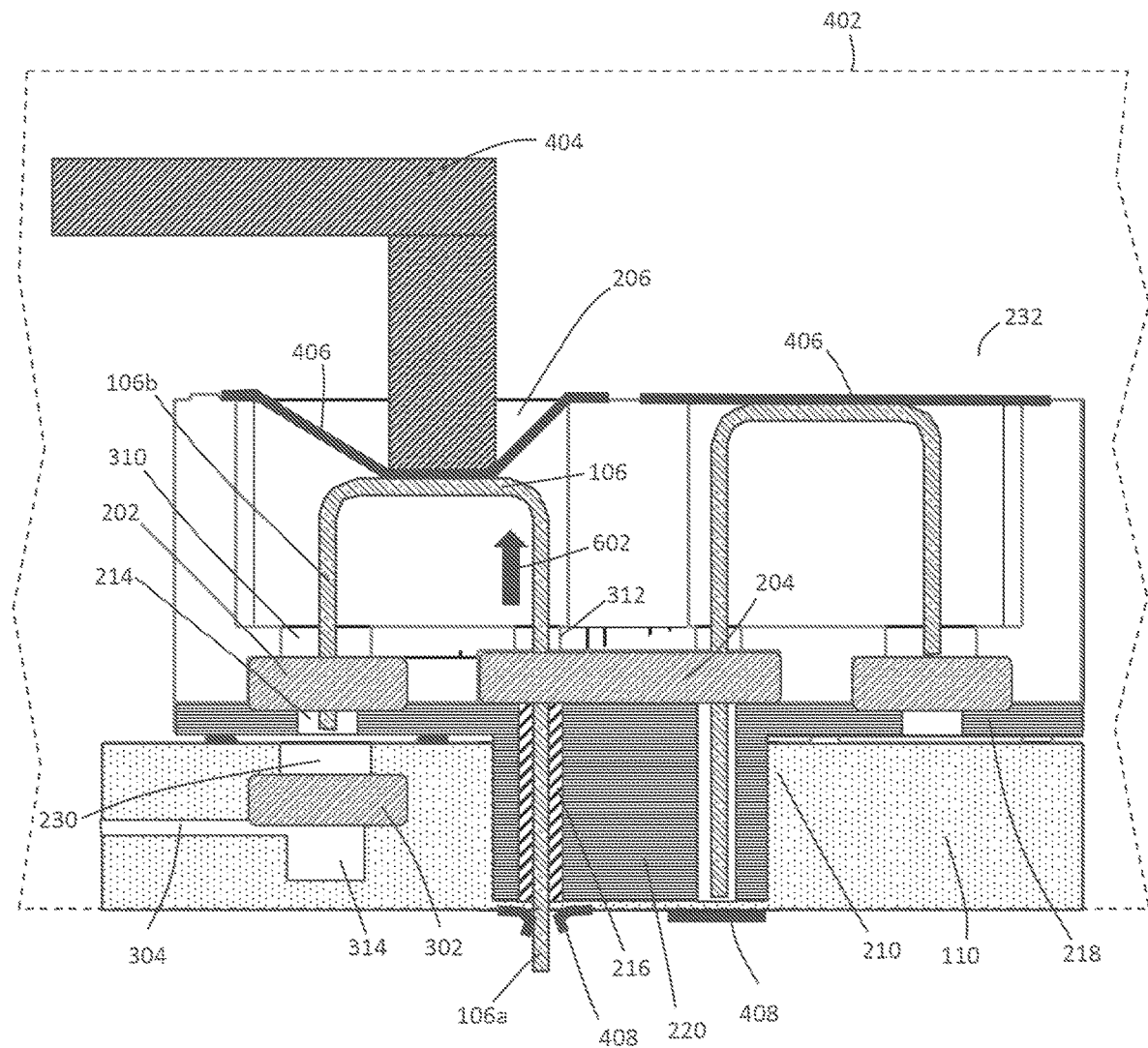
FIG. 6 provides a profile, cross-sectional view of the fluidic subsystem of FIG. 1 as the injection needle is in the process of being withdrawn, but before it has been completely withdrawn, in accordance with at least one embodiment.
Figure 7:
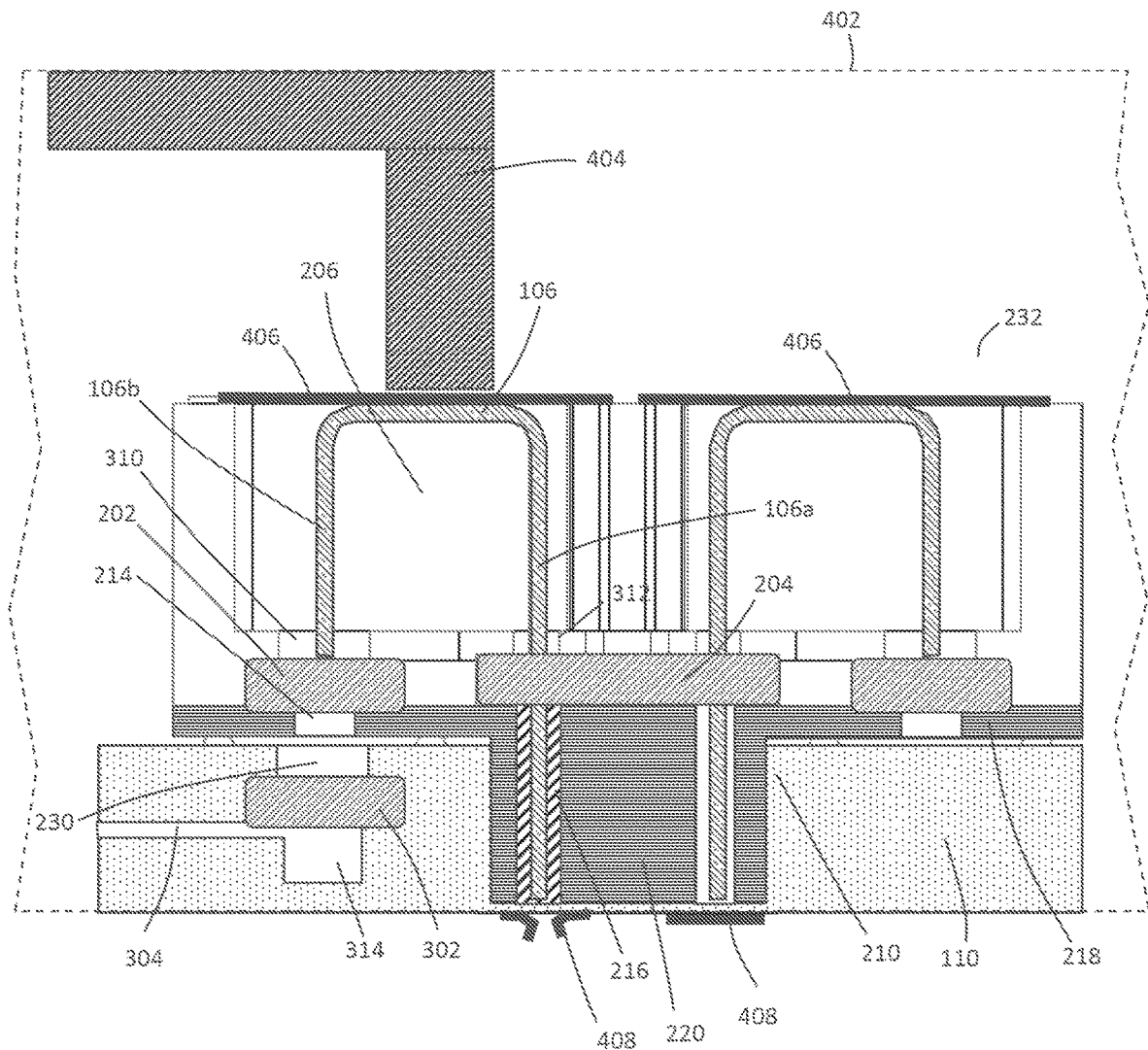
FIG. 7 provides a profile, cross-sectional view of the fluidic subsystem of FIG. 1 when the injection needle has been completely withdrawn after an injection, in accordance with at least one embodiment.

FIG. 6 provides a profile, cross-sectional view of fluidic subsystem 100 as the injection needle is in the process of being withdrawn, but before it has been completely withdrawn. FIG. 7 provides a profile, cross-sectional view of fluidic subsystem 100 when the injection needle has been completely withdrawn. In addition to driving needle assembly 106 downwards, drive assembly 404 may also be configured to withdraw needle assembly 106 upwards in the direction of arrow 602. Examples of suitable drive assemblies and needle assemblies may be found in the previously-mentioned U.S. Pat. No. 8,057,434 and U.S. Patent Application Pub. No. 2010/0152660, both of which are incorporated herein in their entirety. Alternatively, needle assembly 106 may be biased upwards in the direction of arrow 602 by an internal spring disposed within magazine top cavity 206. As needle assembly 106 is drawn upwards, injection needle 106a is drawn out of the patient and back into injection-needle hole 216. At the same time, septum-piercing needle 106b is first drawn out of drug container septum 302, pulled along the intermediate pathway defined by septum-piercing-needle hole 214, inner O-ring 224, outer O-ring 222, and fluid hole 230, and then drawn out of the compartment septum 202 associated with the driven needle assembly.

As needle assembly 106 is drawn up, portions of the injection needle 106a that had previously been extended below injection-needle septum 204, and which had therefore been exposed to external atmosphere during the injection, is drawn into magazine top cavity 206. Such exposed portions may be contaminated by bacteria or other contaminants present in the external atmosphere or environment. As a result, in some cases and in some embodiments, magazine top cavity 206 may no longer be considered sterile after such exposed portions of injection-needle 106a have been withdrawn into the cavity, as indicated by the bolded hashing within magazine top cavity 206. However, compartment septum 202 maintains an air-tight seal between magazine top cavity 206 and the intermediate pathway, thus preserving the sterility of the intermediate pathway.

After a used needle assembly 106 has been completely withdrawn after an injection (as depicted in FIG. 7), needle magazine 104 may then be rotated (e.g., by one or more mechanical gears) to move the used needle assembly out of the way and align a new, sterile needle assembly 106 within another sealed injection-needle compartment 112 with drive assembly 404 and fluid hole 230. In this way, the fluidic subsystem may be configured to use a new needle assembly for each injection of the drug fluid. When each needle assembly in the needle magazine 104 has been used, the compartment septum 202 in each injection-needle compartment 112 will have been pierced only once, but the drug container septum 302 will have been pierced multiple times. Specifically, the drug container septum 302 will have been pierced once for every injection administered by the fluidic subsystem 100, and will have automatically re-sealed after each injection. After every needle assembly in the needle magazine 104 has been used, the entire injection apparatus of which the fluidic subsystem 100 is a part may be discarded. With each injection, the injection-needle septum 204, the compartment septum 202, and the flexible cover 206 work together as described previously to preserve the sterility of the intermediate pathway defined by septum-piercing-needle hole 214, drug-pathway O-ring 226, and fluid hole 230. Preserving the sterility of the intermediate pathway in turn preserves the sterility of the drug fluid pathway defined at least in part by drug fluid chamber 314 and drug fluid conduit 304, as well as of the drug fluid stored in drug container 316. As a result, fluidic subsystem 100 may be used to provide multiple injections over an extended period of time (e.g., multiple days, weeks, or even months) even if the drug fluid stored in drug container 316 is not preserved.

Some embodiments of fluidic subsystem 100 may not include the injection-needle septum 204. As previously-discussed, the injection-needle septum 204 serves to prevent non-sterile, external atmosphere from entering the interior of magazine top cavity 206 when injection needle 106a breaks the frangible sterility film 408. This prevents external atmosphere from contaminating the septum-piercing needle 106b before it is driven through compartment septum 202, the intermediate pathway, and/or the drug container septum 302. However, the period of time between when frangible sterility film 408 is breached and when septum-piercing needle 106b is driven through the compartment septum, the intermediate pathway and/or the drug container septum 302 can be extremely brief. In some cases and in some embodiments, the needle assembly 106 and the drive assembly 404 may be configured to decrease that exposure to an acceptably brief period so as to adequately diminish any contamination risk. For example, the drive assembly 404 may be configured to drive the needle assembly 106 down within a very brief period of time, e.g., on the order of microseconds. In such embodiments, the injection-needle septum 204 may be safely removed.

Some embodiments of fluidic subsystem 100 may also replace flexible cover 406 with a frangible sterility film similar to film 408. Instead of maintaining an air-tight seal when deformed by drive assembly 404, cover 406 may instead be configured to simply tear or rip, thus allowing external atmosphere into magazine top cavity 206 when breached. While this may expose portions of septum-piercing needle 106b to external atmosphere before it is driven through compartment septum 202, the intermediate pathway, and/or the drug container septum 302, the needle assembly 106 and the drive assembly 404 may be configured to decrease that exposure to an acceptably brief period so as to adequately diminish any contamination risk. In some embodiments, fluidic subsystem 100 may omit both injection-needle septum 204 as well as replace flexible cover 406 with a frangible sterility film.

In yet other embodiments, fluidic subsystem 100 may comprise not just one single injection-needle septum 204, but multiple injection-needle septa. For instance, the fluidic subsystem 100 may comprise a separate injection-needle septum for each injection-needle compartment 112a-h, just as there is a separate compartment septum 202 for each compartment 112a-h. In other embodiments, some or all of the compartment septa 202 and/or the injection-needle septum 204 may be replaced by a single sheet of re-sealable elastomer that serves as a single septum.

In some embodiments, the sterility film 408 is not configured to be breached by injection-needle 106a, but is instead configured to be peeled off by the user just prior to actuation of the drive assembly. Such embodiments may include individual peel-off films, each one protecting an individual injection-needle septum 204, or may alternatively include a single peel-off film that protects an integrated needle septum 204, if the commensurate reduction in the sterility of the exposed septa is deemed acceptable.

Figure 8:
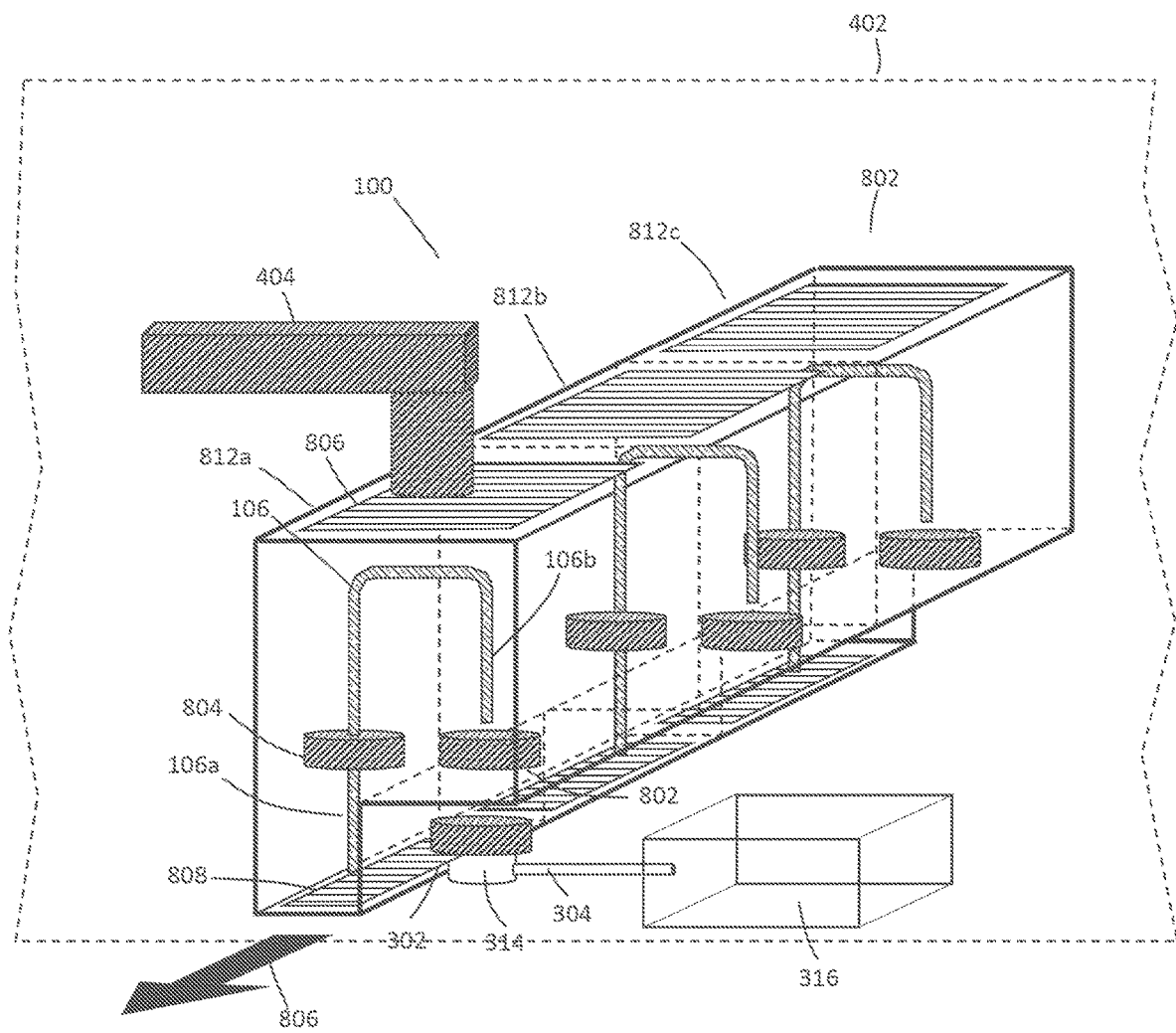
FIG. 8 depicts an alternate embodiment of the fluidic subsystem that comprises a linear magazine, in accordance with at least one embodiment.

In some embodiments of fluidic subsystem 100, the rotatable needle magazine 104 may be replaced by a linear magazine of needles that may be translated over the drug container septum. FIG. 8 depicts one such embodiment. Instead of a round needle magazine 104, this embodiment of fluidic subsystem 100 comprises a linear magazine 802 that comprises a plurality of injection-needle compartments 812a, 812b, and 812c that are arranged along a straight axis in the direction of arrow 806. Similar to the injection-needle comparts 112a-h described above, each injection-needle compartment 812a, 812b, and 812c is sealed in an air-tight manner from each other and from external atmosphere. Each injection-needle compartment 812a-c may also be sterilized during manufacturing and assembly. Although FIG. 8 depicts only three injection needle compartments, there may be more or fewer compartments. Each compartment 812a, 812b, and 812c houses a needle assembly 106 comprising an injection needle 106a and a septum-piercing needle 106b. Each compartment 812a-c also includes a compartment septum 802 (similar to compartment septum 202 described above), and an injection-needle septum 804 (similar to injection-needle septum 204 described above). Also similar to the embodiments discussed above, the top of each injection-needle compartment 812a, 812b, and 812c is covered by a flexible cover 806. Similar to cover 406 described previously, flexible cover 806 may be configured to flex but not break to allow drive assembly 404 to drive needle assembly 106 downwards, while also maintaining an air-tight seal. Alternatively, as discussed previously, flexible cover 806 may be replaced by a frangible sterility film that rips or tears when drive assembly 404 drives needle assembly 106 downwards if the contamination risk is deemed to be acceptably small. The bottom of each injection-needle compartment 812a-c may be covered by a frangible or peelable sterility film 808 similar to frangible or peelable sterility film 408.

A first injection-needle compartment 812a may initially be positioned such that the septum-piercing needle 106b within that compartment is aligned with drug-container septum 302, as shown in FIG. 8. Once aligned, drive assembly 404 may be actuated to drive needle assembly 106 downwards such that septum-piercing needle 106b pierces compartment septum 802, traverses an intermediate pathway, pierces drug container septum 302, and accesses drug fluid chamber 314. The intermediate pathway may be sealed from external atmosphere by rubber seals (not shown) that allow the magazine 802 to translate along the direction of arrow 806 while maintaining an air-tight seal. Similar to previously-described embodiments, drug fluid chamber 314 is in fluid communication with drug container 316 via drug fluid conduit 304. When needle assembly 106 is driven downwards by drive assembly 404, injection-needle 106a breaks sterility film 808, protrudes at least partially out of an outer casing 402, and into a patient (not shown). Alternatively, sterility film 808 may be peeled back by a patient before the needle assembly 106 is driven downwards. By driving needle assembly 106 downwards, a fluid path is thus established between drug container 316 and the patient, allowing a drug fluid from drug container 316 to be pumped or drawn into the patient. After the injection, needle assembly 106 is withdrawn back into injection-needle compartment 812a.

After needle assembly 106 is withdrawn into compartment 812a, the linear magazine 802 may translate in the direction of arrow 806. This translation moves the used compartment 812a out of the way and positions the next compartment 812b in-line with drug container septum 302. The drive assembly 404 may then be used to drive the needle assembly 106 in compartment 812b. When the needle assembly 106 in compartment 812b has completed its injection, the linear magazine 802 may be translated again to position compartment 812c in-line with drug container septum 302. In this way, each step of the linear magazine 802 creates the necessary alignment between the needle assembly 106 in an un-used injection compartment and drug container septum 302. The linear magazine 802 may thus be translated until each compartment 812a-c has been used in an injection. At that point, the linear magazine 802, the fluidic subsystem 100, and/or the drug-delivery apparatus of which fluidic subsystem 100 is a part may be discarded. In some embodiments, the linear magazine 802 may include one or more angled turns to reduce the overall size profile of the subsystem.

While this device has been described as having an exemplary design, the embodiments of the present disclosure may be further modified within the spirit and scope of this disclosure. This application is therefore intended to cover any variations, uses, or adaptations of the disclosed embodiments using its general principles.

The invention claimed is:

1. An apparatus for delivering multiple injections of a pharmaceutical liquid to a patient, comprising:
    a needle magazine including a body defining a plurality of injection needle compartments that are each sealed in an air-tight manner from each other and from external atmosphere, each injection needle compartment comprising (i) a needle assembly having an injection needle and an associated septum piercing needle spaced apart from the injection needle and in fluid communication with the injection needle, and (ii) a compartment septum associated with the needle assembly and configured to be pierced by the septum piercing needle;
    a drug container containing the pharmaceutical liquid, the drug container in fluid communication with a drug fluid pathway;
    a drug container septum that separates the drug fluid pathway from an intermediate pathway that leads to the needle magazine; and
    a drive assembly configured to, when actuated, drive a needle assembly of one of the injection needle compartments such that the injection needle of the driven needle assembly extends from the needle magazine and into a patient, and such that the septum piercing needle of the driven needle assembly pierces the compartment septum associated with the driven needle assembly, traverses the intermediate pathway, and pierces the drug container septum to access the drug fluid pathway, thereby creating a fluid pathway from the drug container to an outlet of the injection needle;
    wherein each injection needle compartment further comprises a separate sterility film that is configured to be peeled away by a user, wherein each sterility film seals each respective injection needle compartment from external atmosphere.

2. The apparatus of claim 1, wherein the compartment septum associated with the driven needle assembly is configured to isolate the intermediate pathway and the drug container septum from atmosphere within the injection needle compartment when the compartment septum associated with the driven needle assembly is pierced by the septum piercing needle.

3. The apparatus of claim 1, wherein the drive assembly is further configured to withdraw the driven needle assembly such that the injection needle of the driven needle assembly is withdrawn out of the patient and the septum piercing needle of the driven needle assembly is withdrawn out of both the drug container septum and the compartment septum associated with the driven needle assembly.

4. The apparatus of claim 3, wherein the needle magazine comprises a round, rotatable body that is configured to rotate after the driven needle assembly has been withdrawn so as to position another needle assembly in another injection needle compartment to be driven by the drive assembly.

5. The apparatus of claim 4, wherein the rotatable body of the needle magazine is disposed on top of a magazine seat that comprises an inner O-ring and an outer O-ring that ensure each injection needle compartment in the needle magazine remains sealed from external atmosphere before use.

6. The apparatus of claim 3, wherein the needle magazine body comprises a linear body that is configured to translate after the driven needle assembly has been withdrawn so as to position another needle assembly in another injection needle compartment to be driven by the drive assembly.

7. The apparatus of claim 1, wherein the compartment septum in each injection needle compartment is configured to be pierced only once before the apparatus is discarded.

8. The apparatus of claim 1, wherein the drug container septum is configured to be pierced multiple times before the apparatus is discarded.

9. The apparatus of claim 1, wherein the drug container septum is configured to be pierced once by the septum piercing needle of the needle assembly in each injection needle compartment before the apparatus is discarded.

10. The apparatus of claim 1, wherein each injection needle compartment, the drug fluid pathway, and the intermediate pathway have been sterilized.

11. The apparatus of claim 1, wherein each injection needle compartment further comprises a flexible cover that is configured to flex but not break to allow the drive assembly to drive the needle assembly in said injection needle compartment while ensuring said needle injection needle compartment remains sealed from external atmosphere.

12. The apparatus of claim 1, wherein each injection needle compartment further comprises a separate frangible sterility film that seals each respective injection needle compartment from external atmosphere, and wherein the drive assembly is configured to drive the driven needle assembly such that the injection needle of the driven needle assembly breaks the frangible sterility film of the injection needle compartment of the driven needle assembly.

13. The apparatus of claim 12, wherein the needle magazine further comprises an injection-needle septum that isolates an interior portion of the injection needle compartment of the driven needle assembly and the septum piercing needle of the driven needle assembly from external atmosphere when the frangible sterility film of the injection needle compartment of the driven needle assembly is broken by the injection needle of the driven needle assembly.

14. The apparatus of claim 1, wherein the pharmaceutical liquid comprises a drug that does not contain any preservatives.

15. The apparatus of claim 1, wherein the pharmaceutical liquid comprises at least one of insulin, an insulin analog, a GLP-1 receptor agonist, glucagon, a glucagon analog, a glucagon derivative, a gastric inhibitory polypeptide (GIP), a GIP analog, a GIP derivative, an oxyntomodulin analog, an oxyntomodulin derivative, a therapeutic antibody, and a therapeutic agent for pain-related treatments.

* * * * *